US012599685B2

(12) United States Patent
Huang et al.

(10) Patent No.: US 12,599,685 B2
(45) Date of Patent: Apr. 14, 2026

(54) TUMOR STROMA IMAGING AGENT AND PREPARATION METHOD THEREOF

(71) Applicant: SHANGHAI UNIVERSITY OF MEDICINE & HEALTH SCIENCES, Shanghai (CN)

(72) Inventors: Gang Huang, Shanghai (CN); Bin Li, Shanghai (CN)

(73) Assignee: SHANGHAI UNIVERSITY OF MEDICINE & HEALTH SCIENCES, Shanghai (CN)

( * ) Notice: Subject to any disclaimer, the term of this patent is extended or adjusted under 35 U.S.C. 154(b) by 759 days.

(21) Appl. No.: 18/016,459

(22) PCT Filed: Oct. 13, 2020

(86) PCT No.: PCT/CN2020/120721
§ 371 (c)(1),
(2) Date: Jan. 17, 2023

(87) PCT Pub. No.: WO2022/032844
PCT Pub. Date: Feb. 17, 2022

(65) Prior Publication Data

US 2023/0277699 A1 Sep. 7, 2023

(30) Foreign Application Priority Data

Aug. 11, 2020 (CN) ......................... 202010801550.9

(51) Int. Cl.
*A61K 51/04* (2006.01)
*A61P 35/00* (2006.01)

(52) U.S. Cl.
CPC .......... *A61K 51/0497* (2013.01); *A61P 35/00* (2018.01)

(58) Field of Classification Search
CPC ............ A61K 51/0497; A61K 31/4709; A61K 51/0459; A61P 35/00; C07D 215/50; C07D 401/12; C07D 401/14; C07F 5/06; C07F 5/069; C07B 2200/05; C07B 2200/07
See application file for complete search history.

(56) References Cited

FOREIGN PATENT DOCUMENTS

| | | |
|---|---|---|
| CN | 102123739 A | 7/2011 |
| CN | 108187078 A | 6/2018 |
| WO | 2019154886 A1 | 8/2019 |

OTHER PUBLICATIONS

William J. McBride, et al., Radiofluorination using aluminum-fluoride (Al18F), EJNMMI Research, 2013, pp. 1-11, vol. 3, No. 36.

Giesel FL, et al., Biodistribution, radiation dosimetry and tumor detection of 18 F-AIF-labeled FAPI-PET /CT in lung cancer patients, NuklearMedizin, 2020, pp. 88,114, vol. 59.

Frederik L. Giesel, et al., FAPI-74 PET/CT Using Either 18F-AIF or Cold-Kit 68Ga Labeling: Biodistribution, Radiation Dosimetry, and Tumor Delineation in Lung Cancer Patients, The Journal of Nuclear Medicine, 2021, pp. 201-207, vol. 62, No. 2.

Eduardo Ruivo, et al., Improved stability of a novel fluorine-18 labeled TCO analogue for pretargeted PET imaging, Nuclear Medicine and Biology, 2019, pp. 36-42, vol. 76-77.

Frederik L. Giesel, et al., 68Ga-FAPI PET/CT: Biodistribution and Preliminary Dosimetry Estimate of 2 DOTA-Containing FAP-Targeting Agents in Patients with Various Cancers, The Journal of Nuclear Medicine, 2019, pp. 386-392, vol. 60, No. 3.

Thomas Lindner, et al., Development of Quinoline-Based Theranostic Ligands for the Targeting of Fibroblast Activation Protein, The Journal of Nuclear Medicine, 2018, pp. 1415-1422, vol. 59, No. 9.

Haojun Chen, et al., Usefulness of [68Ga]Ga-DOTA-FAPI-04 PET/CT in patients presenting with inconclusive [18F] FDG PET/CT findings, European Journal of Nuclear Medicine and Molecular Imaging, 2020.

*Primary Examiner* — Robert S Cabral
(74) *Attorney, Agent, or Firm* — Bayramoglu Law Offices LLC

(57) ABSTRACT

A tumor stroma imaging agent with a chemical structural formula (I):

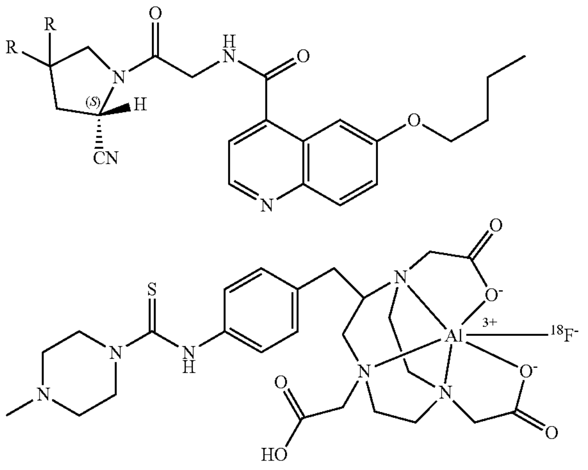

is provided, where R is hydrogen or fluorine. Compared with the prior art, the tumor stroma imaging agent exhibits significant affinity for fibroblast activation protein (FAP), high uptake for a malignant tumor with high FAP expression in a tumor stroma, and high sensitivity and specificity for the diagnosis of a malignant tumor, and is not prone to false positives. Therefore, the tumor stroma imaging agent can be effectively and safely used for the diagnosis and treatment of various malignant tumors with a prolonged half-life and an extended window period, which is conducive to clinical application.

15 Claims, 1 Drawing Sheet

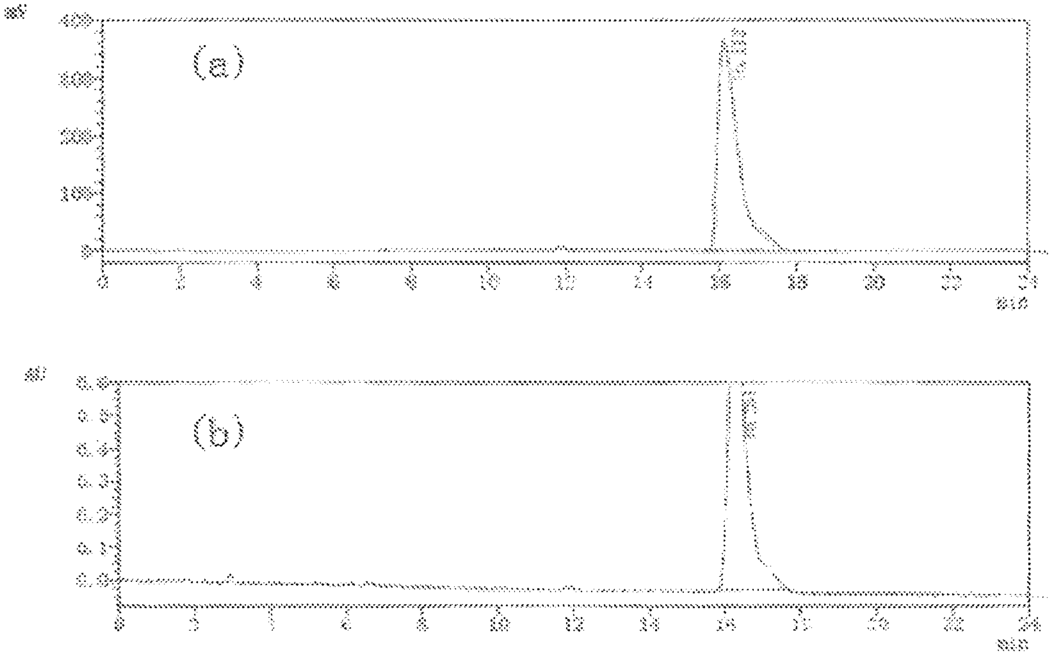
(a)
(b)

TUMOR STROMA IMAGING AGENT AND PREPARATION METHOD THEREOF

CROSS REFERENCE TO THE RELATED APPLICATIONS

This application is the national phase entry of International Application No. PCT/CN2020/120721, filed on Oct. 13, 2020, which is based upon and claims priority to Chinese Patent Application No. 202010801550.9, filed on Aug. 11, 2020, the entire contents of which are incorporated herein by reference.

TECHNICAL FIELD

The present disclosure belongs to the technical field of nuclear medicine and specifically relates to a tumor stroma imaging agent and a preparation method thereof.

BACKGROUND

Tumor stroma is a general term for components other than tumor cells in tumor tissue, including cellular components (mesenchymal cells) and non-cellular components. The interaction of a tumor stroma and a tumor cell determines the biological behaviors of a tumor (growth, infiltration, metastasis, or the like). A tumor-stroma reaction refers to the formation of a stromal microenvironment favorable for promoting tumor progression during tumorigenesis, which is accompanied by the activation of fibroblasts and the expression of fibroblast activation protein (FAP). FAP is a type II transmembrane serine protease (TTSP) specifically expressing on a membrane surface of cancer-associated fibroblasts (CAFs), in which cytoplasmic, transmembrane, and extracellular domains include 6, 18, and 736 amino acids, respectively. FAP is selectively expressed in 90% or more of stromata of malignant epithelial tumors (such as breast cancer, ovarian cancer, lung cancer, colon cancer, pancreatic cancer, cutaneous melanoma, kidney cancer, bladder cancer, rectal cancer, cervical cancer, non-small cell lung cancer, and hepatocellular carcinoma (HCC)), embryonic tissues, healing wounds, and physiologically-reconstructed organs but is generally not expressed in normal adult tissues.

Talabostat (PT-100) with a chemical name of [(2R)-1-[(2S)-2-amino-3-methylbutanoyl]pyrrolidin-2-yl]boronic acid (CAS No. 149682-77-9) (namely, Val-Boro-Pro) has a structural formula as follows:

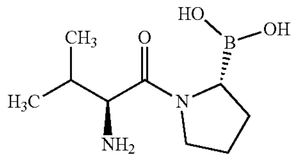

Val-Boro-Pro (chemical name: PT-100 or Talabostat)

Val-Boro-Pro is the first studied competitive inhibitor with a high affinity for FAP. However, in patients with metastatic colon cancer, non-small cell lung cancer, and melanoma, either the administration of PT-100 alone or the administration of PT-100 in combination with other nonspecific anti-tumor drugs leads to unsatisfactory clinical efficacy. In 2019, the improvement results of PT-100 were reported by Clemens Kratochwil et al. in the *Journal of Nuclear Medicine* (2019, 60 (3), pp. 386-392), where PT-100 was modified with quinoline, and two preferred compounds were screened out and labeled with a radionuclide $^{68}$Ga emitting positron to prepare positron imaging agents $^{68}$Ga-FAPI-4 and $^{68}$Ga-FAPI-2 (with structural formulas as follows), which successfully realized the positron emission tomography/computed tomography (PET/CT) imaging for primary and metastatic foci of 28 malignant tumors in patients. In 2020, a gain value of [$^{68}$Ga]Ga-DOTA-FAPI-4 PET/CT imaging for $^{18}$F-FDG PET/CT non-deterministic manifestations was further reported in the European *Journal of Nuclear Medicine* and Molecular Imaging (DOI: https://doi.org/10.1007/s00259-020-04940-6).

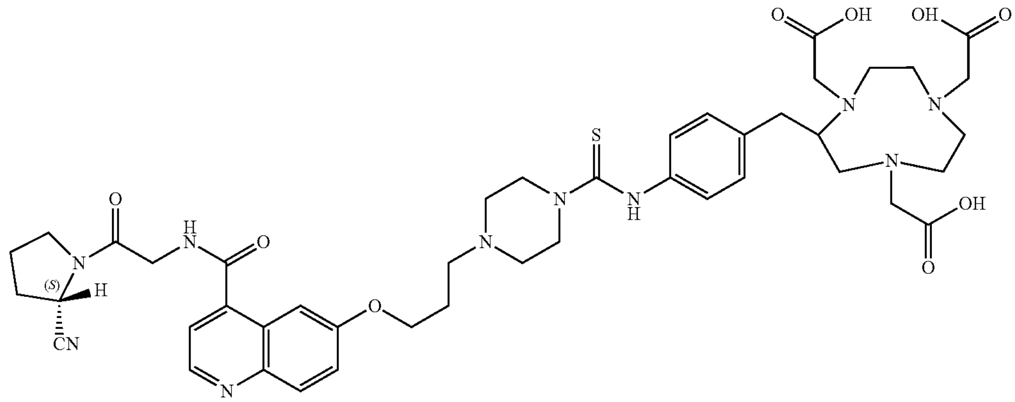

68Ga-FAPI-2

-continued

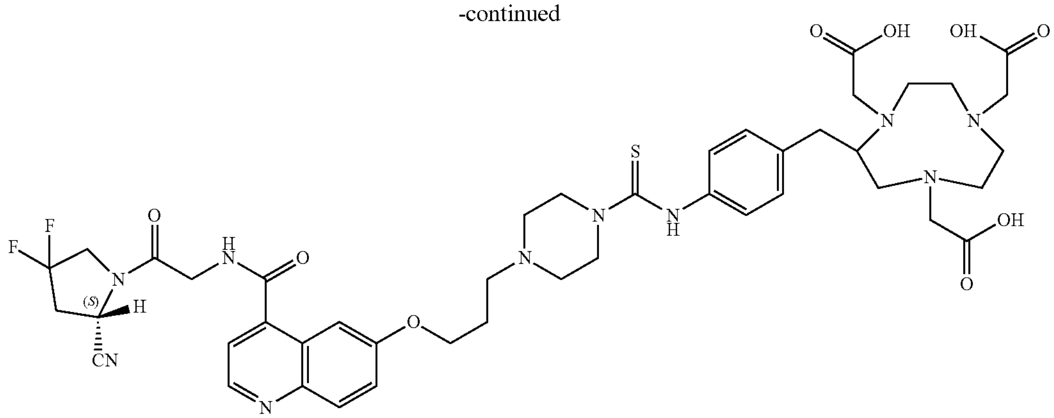

68Ga-FAPI-4

Although it has been confirmed that $^{68}$Ga-FAPI-4 can be used for tumor imaging, the liquid target bombardment of a $^{68}$Ga/$^{68}$Ge generator or cyclotron is required to acquire $^{68}$Ga due to its relatively short half-life (68 min) and toxicity, and most positron emission tomography (PET) centers in China do not enable the above condition, which limits the clinical application.

SUMMARY

Through extensive and in-depth research, the inventors further modify the structures of $^{68}$Ga-FAPI-4 and $^{68}$Ga-FAPI-2 to screen out small-molecule ligands capable of specifically binding to FAP, and on this basis, an isotope-labeled imaging agent specifically targeting FAP is developed. The specific small-molecule ligands of the present disclosure exhibit significant affinity for FPA, and thus, can be effectively and safely used for the diagnosis and treatment of various malignant tumors. On this basis, the present disclosure is implemented.

The present disclosure is intended to provide a tumor stroma imaging agent with high sensitivity and specificity and a preparation method thereof.

The tumor stroma imaging agent provided in the present disclosure has a chemical structural formula as follows:

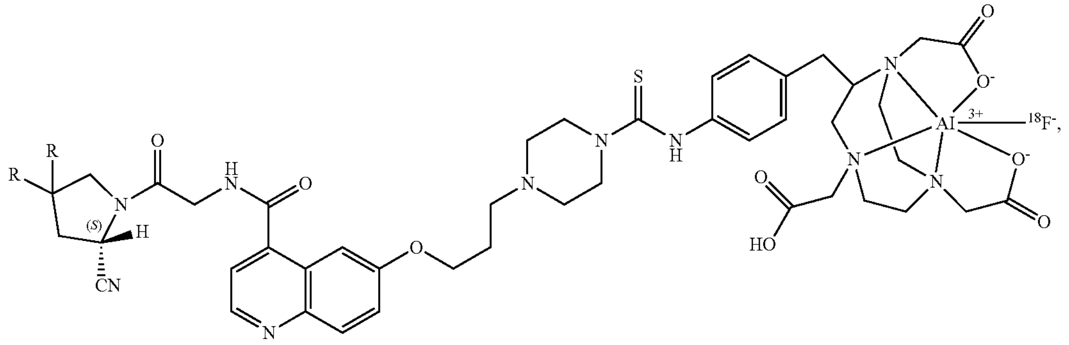

where R is hydrogen or fluorine.

As a preferred technical solution, the tumor stroma imaging agent has a chemical structural formula as follows:

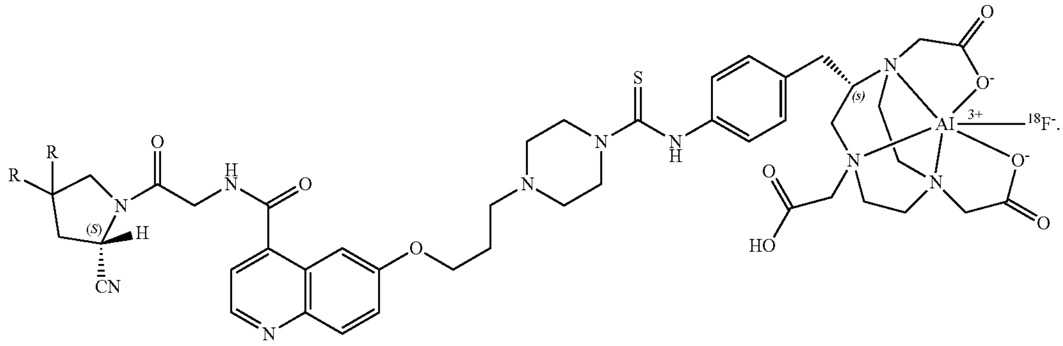

A preparation method of the tumor stroma imaging agent according to the present disclosure is provided, including the following steps:

mixing an $^{18}F$-containing acetic acid-sodium acetate buffer with a labeling precursor, a solvent, and an $AlCl_3$ aqueous solution to allow a labeling reaction; and subjecting a product of the labeling reaction to a post-treatment, where the labeling precursor has a chemical structural formula as follows:

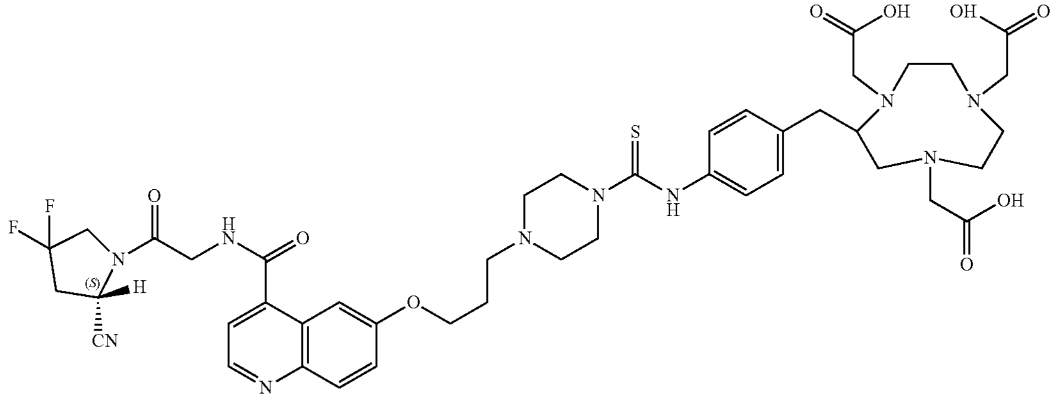

or a salt thereof.

The $^{18}F$-containing acetic acid-sodium acetate buffer can be prepared as follows:

conducting an $^{18}O(p, n)^{18}F$ reaction with a proton cyclotron to produce $^{18}F^-$; transporting the generated $^{18}F^-$ through a pipe to an anion exchange column QMA for capture; and after the capture is completed, blow-drying the QMA with $N_2$ and rinsing the QMA with an acetic acid-sodium acetate buffer for elution to obtain the $^{18}F$-containing acetic acid-sodium acetate buffer.

As a preferred technical solution, the $^{18}F$-containing acetic acid-sodium acetate buffer has an activity of 110 mCi to 135 mCi and a pH of 4.2, and the anion exchange column QMA is a refillable column.

An activity of $^{18}F^-$ generated by the $^{18}O(p, n)^{18}F$ reaction is controlled from 120 mCi to 160 mCi.

Preferably, the labeling reaction is conducted at 80° C. to 120° C. for 5 min to 10 min under the following conditions: a volume-mass ratio of the $^{18}F$-containing acetic acid-sodium acetate buffer to the labeling precursor is 1:(0.9-1.6) mL/mg; the $AlCl_3$ aqueous solution has a concentration of 0.4 M; the $^{18}F$-containing acetic acid-sodium acetate buffer, the solvent, and the $AlCl_3$ aqueous solution are in a volume ratio of (45-30):75:5; the $AlCl_3$ aqueous solution has a concentration of 0.4 M; and the solvent is selected from the group consisting of acetonitrile, N,N-dimethylformamide (DMF), dimethylsulfoxide (DMSO), and polyethylene glycol (PEG).

After the labeling reaction is complete, a product of the labeling reaction is subjected to a post-treatment to obtain an injection of the tumor stroma imaging agent that can be used for the diagnosis of a tumor.

The post-treatment specifically includes:

adding water to quench the labeling reaction and allowing the resulting reaction solution to pass through an $Al_2O_3$ column to obtain a filtrate; and allowing the filtrate to pass through a $C_{18}$-Plus column, rinsing the column with ethanol and normal saline (NS) successively, and allowing an eluate to pass through a sterile filtration membrane to obtain an injection of the tumor stroma imaging agent.

The water can be added at an amount of 10 to 20 times the volume of the $^{18}F^-$-containing acetic acid-sodium acetate buffer to quench the labeling reaction.

The injection has an activity of 50.3 mCi to 72.3 mCi.

A typical reaction route of the present disclosure is as follows:

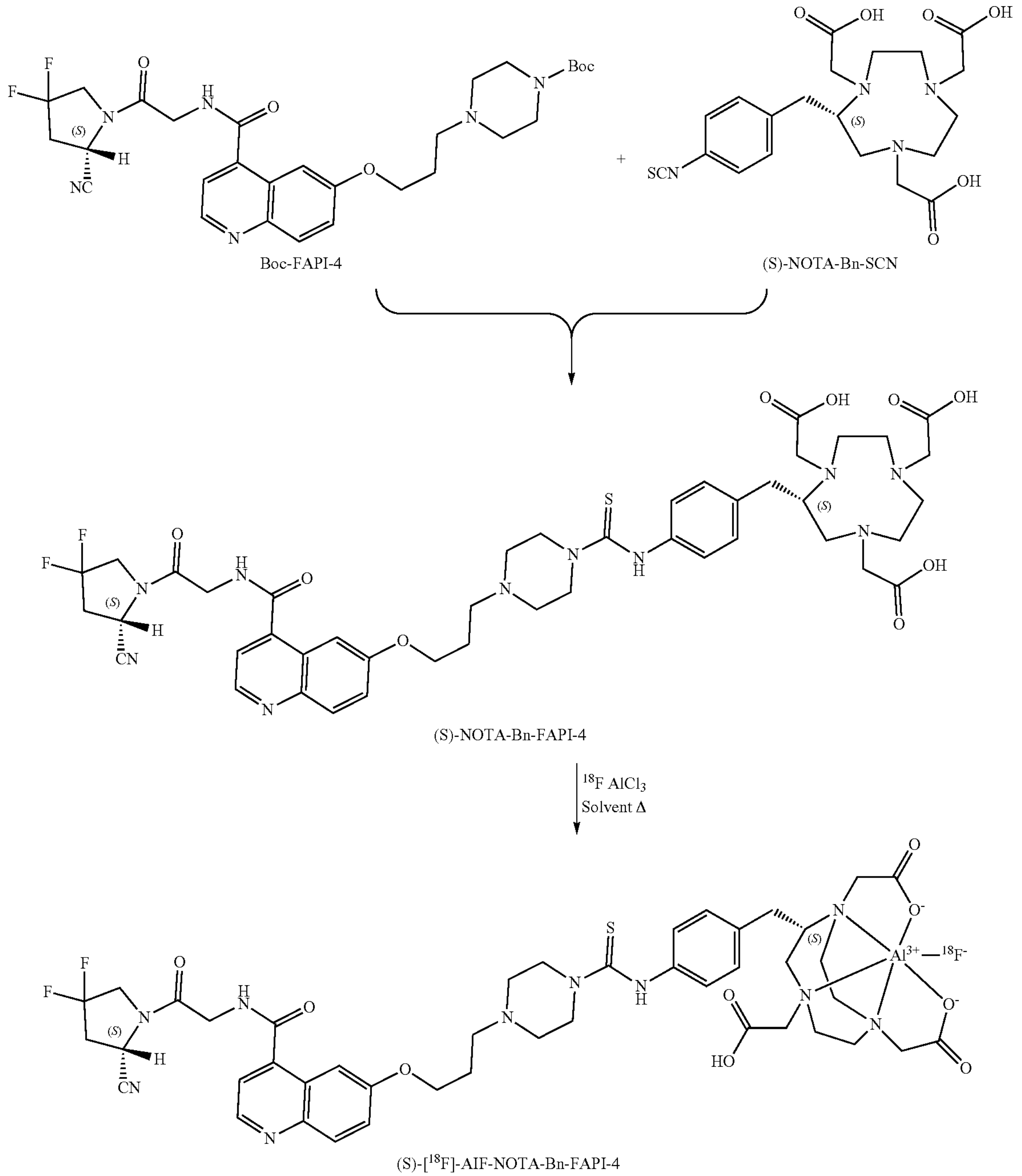

Boc-FAPI-4

(S)-NOTA-Bn-SCN (S)-NOTA-Bn-FAPI-4

(S)-[$^{18}$F]-AlF-NOTA-Bn-FAPI-4

There is a large amount of stroma in most malignant tumor foci, especially in breast cancer, colon cancer, pancreatic cancer, etc., with strong fibroproliferative responses. In these tumor foci, mesenchymal cells account for about 90% and tumor cells account for only about 10%. CAFs highly expressing FAP are the main component of tumor stroma. Given the abundant stroma in malignant tumor foci and the dominated CAFs highly expressing FAP in the stroma, FAP as a specific marker of CAFs is expected to become a promising tumor imaging and treating target. Although the initial competitive inhibitor PT-100 with high affinity for FAP enzymatic activity fails to achieve an ideal clinical effect, a new competitive inhibitor obtained by modifying PT-100 with a quinoline structure shows an affinity for FAP enzymatic activity that is increased by 60 times and reaches a 10 nmol level. After being labeled with a nuclide, the new competitive inhibitor can successfully achieve PET/CT imaging in 28 malignant tumors and leads to non-deterministic PET manifestations (there is low or no uptake of $^{18}$F-FDG in foci or uptake in a focus is similar to an uptake in the surrounding normal tissue, thus resulting in an unclear display). The new FAP inhibitor imaging agent has superior clinical performance.

The present disclosure has the following beneficial effects:

1. In the present disclosure, Boc-FAPI-2 and Boc-FAPI-4 each are modified with (S)-NOTA-Bn-SCN instead of the bifunctional chelating agent DOTA, which involves a simplified labeling process. (S)—[$^{18}$F]—AlF-NOTA-Bn-FAPI-4 is an improved new PET/CT molecular probe targeting tumor stromal fibroblasts.

2. In the present disclosure, a new tumor stroma diagnostic imaging agent (S)—[$^{18}$F]—AlF-NOTA-Bn-FAPI-4 is obtained through $^{18}$F labeling, which is conducive to clinical application. Since $^{18}$F has a half-life of 120 min and $^{68}$Ga has a half-life of 68 min, the tumor stroma-targeted diagnostic imaging agent (S)—[$^{18}$F]—AlF-NOTA-Bn-FAPI-4 has an extended window period and improved safety, and thus can be widely used in clinical tumor stroma-targeted imaging to achieve accurate preoperative staging for early malignant tumors and effective early radical treatment of tumors.

FIG. 1B shows an HPLC spectrum of (S)—AlF-NOTA-Bn-FAPI-4 control prepared in Example 11.

DETAILED DESCRIPTION OF THE EMBODIMENTS

The present disclosure is further described in detail below in conjunction with specific examples and by referring to data. It should be understood that the examples are provided to merely illustrate the present disclosure and do not limit the scope of the present disclosure in any way.

Example 1

Preparation of (S)—[$^{18}$F]—AlF-NOTA-Bn-FAPI-4

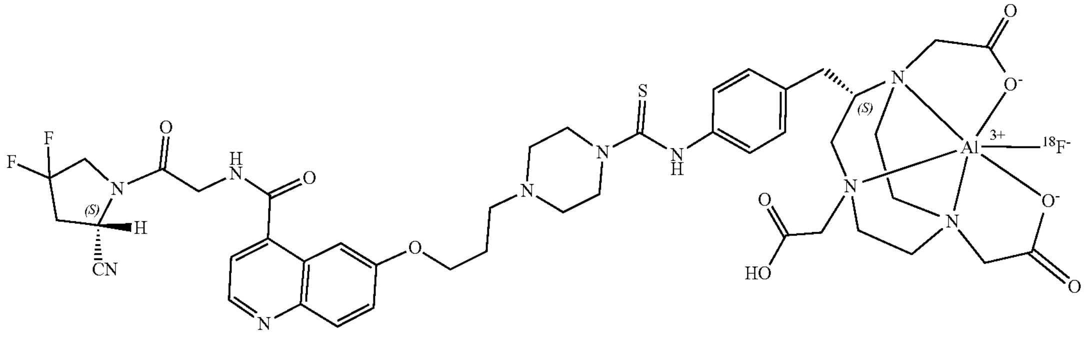

(S)-[$^{18}$F]-AlF-NOTA-Bn-FAPI-4

3. In the present disclosure, given a close correlation between FAP in tumor stroma and a corresponding malignant tumor, Boc-FAPI-4 is labeled with Al—$^{18}$F to obtain a new tumor stroma-targeted diagnostic imaging agent (S)—[$^{18}$F]—AlF-NOTA-Bn-FAPI-4, which enables the imaging and positioning of primary and metastatic tumor foci through preoperative PET/CT imaging. The diagnostic imaging agent exhibits excellent pharmacokinetic properties, high uptake for a malignant tumor with high FAP expression in the tumor stroma, and high sensitivity and specificity in the diagnosis of a malignant tumor and is not prone to false positives.
4. The inhibitor (S)—AlF-NOTA-Bn-FAPI-4 for FAP in the tumor stroma provided by the present disclosure can significantly accumulate at a tumor site and delay tumor growth, and can also achieve imaging through a radionuclide. Therefore, the inhibitor not only has a therapeutic value in FAP-positive tumors but also helps reveal the specific biological behaviors of FAP in the tumor stroma and tumorigenesis.
5. Compared with the existing $^{68}$Ga-FAPI-4 and $^{68}$Ga-FAPI-2, the present disclosure introduces lipophilic aryl (Bn-SCN) between the chelating agent and the quinoline, which improves the absorption of the imaging agent in a tissue, thereby acquiring a prominent imaging effect.

BRIEF DESCRIPTION OF THE DRAWINGS

FIG. 1A shows a high-performance liquid chromatography (HPLC) spectrum of (S)—[$^{18}$F]—AlF-NOTA-Bn-FAPI-4 prepared in Example 1.

An $^{18}$O(p, n)$^{18}$F reaction was conducted with a proton cyclotron to produce $^{18}F^-$ with an activity of 150 mCi. The generated $^{18}F^-$ was transported through a pipe to an anion exchange column QMA (QMA was a refillable column) for capture. After the capture was completed, the QMA was blow-dried with $N_2$ and then rinsed with 0.45 mL of an acetic acid-sodium acetate buffer at a pH of 4.2 for elution to obtain an $^{18}$F-containing buffer with an activity of 135 mCi.

469.7 μg of a labeling precursor (S)-NOTA-Bn-FAPI-4, 0.75 mL of acetonitrile, and 0.05 mL of a 0.4 M $AlCl_3$ aqueous solution were added to 0.45 mL of the $^{18}$F-containing buffer to allow a reaction at 80° C. for 10 min, and 5 mL of deionized water was added to quench the reaction. The resulting reaction solution was allowed to pass through an $Al_2O_3$ column to obtain a filtrate.

The filtrate was allowed to pass through a $C_{18}$-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-4 with an activity of 72.3 mCi and a labeling rate of 48.2%.

The retention time and radiochemical purity of (S)—[$^{18}$F]—AlF-NOTA-Bn-FAPI-4 were tested by HPLC, and test results are shown in FIGS. 1A-1B. The peak time of (S)—[$^{18}$F]—AlF-NOTA-Bn-FAPI-4 is 16.112 min, which is consistent with a retention time of the (S)—AlF-NOTA-Bn-FAPI-4 control, and the radiochemical purity is still as high as 99% after labeling.

Example 2

An $^{18}$O(p, n)$^{18}$F reaction was conducted with a proton cyclotron to produce $^{18}F^-$ with an activity of 150 mCi. The generated $^{18}F^-$ was transported through a pipe to an anion exchange column QMA (QMA was a refillable column) for capture. After the capture was completed, the QMA was blow-dried with $N_2$ and rinsed with 0.3 mL of an acetic acid-sodium acetate buffer at a pH of 4.2 for elution to obtain an $^{18}F^-$-containing buffer with an activity of 125 mCi.

469.7 μg of a labeling precursor (S)-NOTA-Bn-FAPI-4, 0.75 mL of acetonitrile, and 0.05 mL of a 0.4 M $AlCl_3$ aqueous solution were added to 0.3 mL of the $^{18}F^-$-containing buffer to allow a reaction at 80° C. for 10 min, and 5 mL of deionized water was added to quench the reaction. The resulting reaction solution was allowed to pass through an $Al_2O_3$ column to obtain a filtrate.

The filtrate was allowed to pass through a $C_{18}$-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-4 with an activity of 67.5 mCi.

Example 3

An $^{18}O(p, n)^{18}F$ reaction was conducted with a proton cyclotron to produce $^{18}F^-$ with an activity of 160 mCi. The generated $^{18}F^-$ was transported through a pipe to an anion exchange column QMA (QMA was a refillable column) for capture. After the capture was completed, the QMA was blow-dried with $N_2$ and rinsed with 0.45 mL of an acetic acid-sodium acetate buffer at a pH of 4.2 for elution to obtain an $^{18}F^-$-containing buffer with an activity of 135 mCi.

469.7 μg of a labeling precursor (S)-NOTA-Bn-FAPI-4, 0.75 mL of acetonitrile, and 0.05 mL of a 0.4 M $AlCl_3$ aqueous solution were added to 0.45 mL of the $^{18}F^-$-containing buffer to allow a reaction at 80° C. for 10 min, and 5 mL of deionized water was added to quench the reaction. The resulting reaction solution was allowed to pass through an $Al_2O_3$ column to obtain a filtrate.

The filtrate was allowed to pass through a Cis-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-4 with an activity of 72 mCi.

Example 4

An $^{18}O(p, n)^{18}F$ reaction was conducted with a proton cyclotron to produce $^{18}F^-$ with an activity of 150 mCi. The generated $^{18}F^-$ was transported through a pipe to an anion exchange column QMA (QMA was a refillable column) for capture. After the capture was completed, the QMA was blow-dried with $N_2$ and rinsed with 0.45 mL of an acetic acid-sodium acetate buffer at a pH of 4.2 for elution to obtain an $^{18}F^-$-containing buffer with an activity of 135 mCi.

469.7 μg of a labeling precursor (S)-NOTA-Bn-FAPI-4, 0.75 mL of acetonitrile, and 0.05 mL of a 0.4 M $AlCl_3$ aqueous solution were added to 0.45 mL of the $^{18}F^-$-containing buffer to allow a reaction at 100° C. for 10 min, and 5 mL of deionized water was added to quench the reaction. The resulting reaction solution was allowed to pass through an $Al_2O_3$ column to obtain a filtrate.

The filtrate was allowed to pass through a Cis-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-4 with an activity of 70 mCi.

Example 5

An $^{18}O(p, n)^{18}F$ reaction was conducted with a proton cyclotron to produce $^{18}F^-$ with an activity of 120 mCi. The generated $^{18}F^-$ was transported through a pipe to an anion exchange column QMA (QMA was a refillable column) for capture. After the capture was completed, the QMA was blow-dried with $N_2$ and rinsed with 0.45 mL of an acetic acid-sodium acetate buffer at a pH of 4.2 for elution to obtain an $^{18}F^-$-containing buffer with an activity of 110 mCi.

469.7 μg of a labeling precursor (S)-NOTA-Bn-FAPI-4, 0.75 mL of acetonitrile, and 0.05 mL of a 0.4 M $AlCl_3$ aqueous solution were added to 0.45 mL of the $^{18}F^-$-containing buffer to allow a reaction at 80° C. for 10 min, and 5 mL of deionized water was added to quench the reaction. The resulting reaction solution was allowed to pass through an $Al_2O_3$ column to obtain a filtrate.

The filtrate was allowed to pass through a $C_{18}$-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-4 with an activity of 53.9 mCi.

Example 6

Preparation of (S)—[$^{18}$F]—AlF-NOTA-Bn-FAPI-2

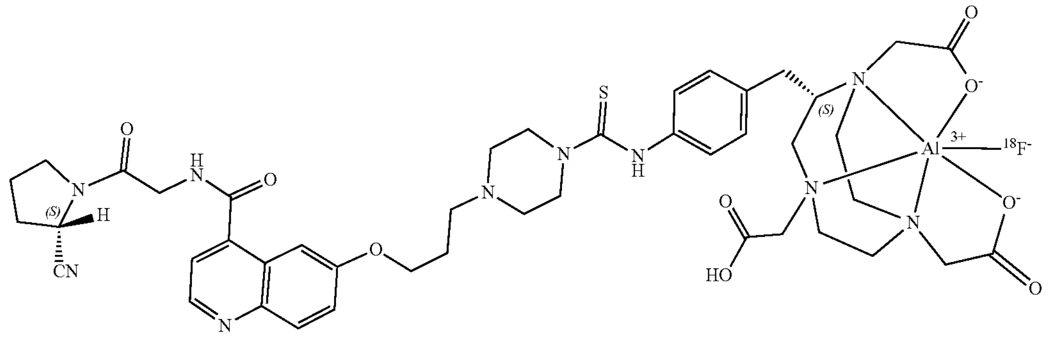

(S)-[$^{18}$F]-AlF-NOTA-Bn-FAPI-2

An $^{18}O(p, n)^{18}F$ reaction was conducted with a proton cyclotron to produce $^{18}F^-$ with an activity of 120 mCi. The generated $^{18}F^-$ was transported through a pipe to an anion exchange column QMA (QMA was a refillable column) for capture. After the capture was complete, the QMA was blow-dried with $N_2$ and rinsed with 0.45 mL of an acetic acid-sodium acetate buffer at a pH of 4.2 for elution to obtain an $^{18}F^-$-containing buffer with an activity of 110 mCi.

433.7 μg of a labeling precursor (S)-NOTA-Bn-FAPI-2, 0.75 mL of DMSO, and 0.05 mL of a 0.4 M $AlCl_3$ aqueous solution were added to 0.45 mL of the $^{18}F^-$-containing buffer to allow a reaction at 100° C. for 8 min, and 5 mL of deionized water was added to quench the reaction. The resulting reaction solution was allowed to pass through an $Al_2O_3$ column to obtain a filtrate.

The filtrate was allowed to pass through a $C_{18}$-Plus column for enrichment, and the column was rinsed with 2 mL of ethanol and 10 mL of NS successively. An eluate was allowed to pass through a sterile filtration membrane to obtain an injection of a tumor stroma diagnostic imaging agent (S)—[$^{18}$F]—AlF-NOTA-Bn-FAPI-2 with an activity of 50.5 mCi.

Example 7

Preparation of [$^{18}$F]—AlF-NOTA-Bn-FAPI-2

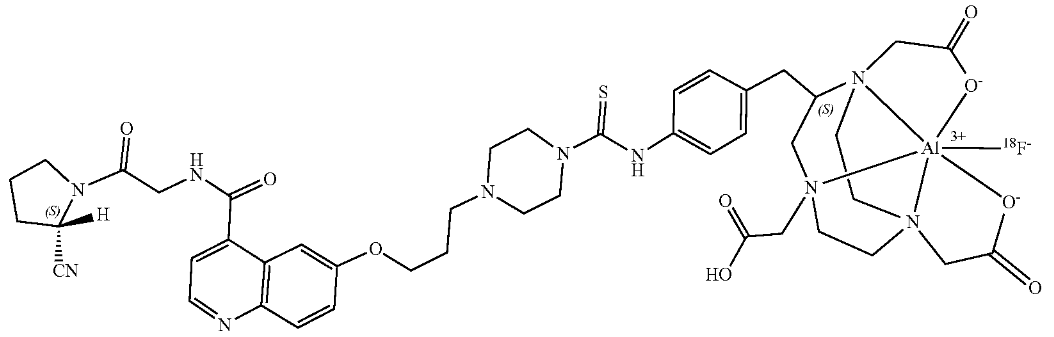

[$^{18}$F]-AlF-NOTA-Bn-FAPI-2

An $^{18}O(p, n)^{18}F$ reaction was conducted with a proton cyclotron to produce $^{18}F^-$ with an activity of 120 mCi. The generated $^{18}F^-$ was transported through a pipe to an anion exchange column QMA (QMA was a refillable column) for capture, and after the capture was completed, the QMA was blow-dried with $N_2$ and then rinsed with 0.45 mL of an acetic acid-sodium acetate buffer at a pH of 4.2 for elution to obtain an $^{18}F$-containing buffer with an activity of 110 mCi.

469.7 μg of a labeling precursor NOTA-Bn-FAPI-2, 0.75 mL of DMF, and 0.05 mL of a 0.4 M $AlCl_3$ aqueous solution were added to 0.45 mL of the $^{18}F^-$-containing buffer to allow a reaction at 110° C. for 8 min, then 5 mL of deionized water was added to quench the reaction, and a resulting reaction solution was allowed to pass through an $Al_2O_3$ column to obtain a filtrate.

The filtrate was allowed to pass through a $C_{18}$-Plus column for enrichment, then the column was rinsed with 2 mL of ethanol and 10 mL of NS successively, and an eluate was allowed to pass through a sterile filtration membrane to obtain an injection of a tumor stroma diagnostic imaging agent [$^{18}$F]—AlF-NOTA-Bn-FAPI-2 with an activity of 50.3 mCi.

Example 8

Preparation of [$^{18}$F]—AlF-NOTA-Bn-FAPI-4

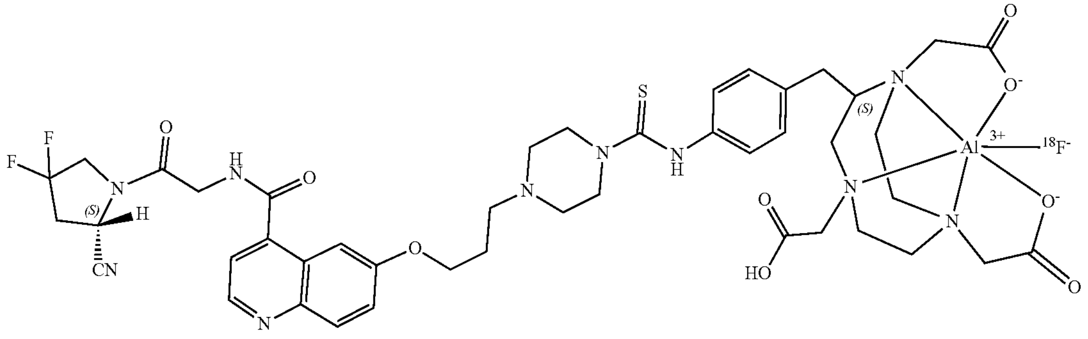

[$^{18}$F]-AlF-NOTA-Bn-FAPI-4

An $^{18}O(p, n)^{18}F$ reaction was conducted with a proton cyclotron to produce $^{18}F^-$ with an activity of 120 mCi, the generated $^{18}F^-$ was transported through a pipe to an anion exchange column QMA (QMA was a refillable column) for capture. After the capture was complete, the QMA was blow-dried with $N_2$ and rinsed with 0.45 mL of an acetic acid-sodium acetate buffer at a pH of 4.2 for elution to obtain an $^{18}F^-$-containing buffer with an activity of 110 mCi.

433.7 Kg of a labeling precursor NOTA-Bn-FAPI-4, 0.75 mL of PEG, and 0.05 mL of a 0.4 M $AlCl_3$ aqueous solution were added to 0.45 mL of the $^{18}F^-$-containing buffer to allow a reaction at 120° C. for 5 min, and 5 mL of deionized water was added to quench the reaction. The resulting reaction solution was allowed to pass through an $Al_2O_3$ column to obtain a filtrate.

The filtrate was allowed to pass through a Cis-Plus column for enrichment, and the column was rinsed with 2 mL of ethanol and 10 mL of NS successively. An eluate was allowed to pass through a sterile filtration membrane to obtain an injection of a tumor stroma diagnostic imaging agent [$^{18}F$]—AlF-NOTA-Bn-FAPI-4 with an activity of 54.5 mCi.

Example 9

Preparation of Boc-FAPI-4 and Boc-FAPI-2

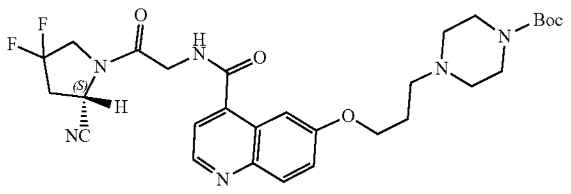

Boc-FAPI-4

-continued

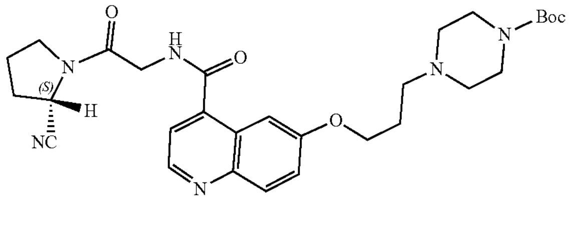

Boc-FAPI-2

The preparation of Boc-FAPI-4 and Boc-FAPI-2 may be conducted by referring to: Thomas Lindner et al. Development of Quinoline-Based Theranostic Ligands for the Targeting of Fibroblast Activation Protein. *Journal of Nuclear Medicine,* 2018, 59 (9), pp. 1415-1422; or may be commercially available. (S)-NOTA-Bn-SCN may be commercially available.

Example 10

Preparation of (S)-NOTA-Bn-FAPI-4

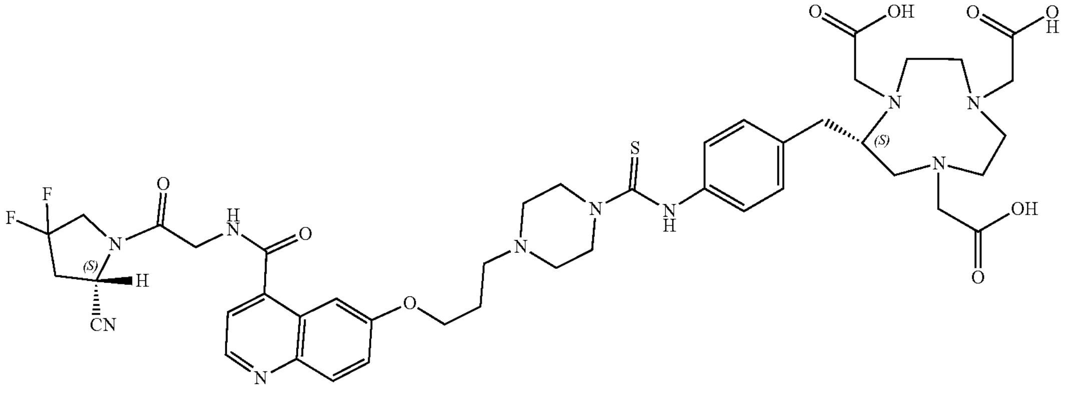

(S)-NOTA-Bn-FAPI-4

21.0 mg (33.9 μmol) of Boc-FAPI-4, 2,200 μL of acetonitrile, and 60.0 mg of p-toluenesulfonic acid were added to a 4 mL reaction flask, heated to 45° C., and stirred to allow a reaction for 2 h. The resulting reaction system was subjected to vacuum distillation to remove the solvent, and a residue was dissolved with 1,050 μL of DMSO to obtain a reaction product solution. 15.0 mg (33.2 μmol) of (S)-NOTA-Bn-SCN was dissolved in 110 μL of DMSO and added to the reaction product solution. The resulting mixed solution was subjected to an ultrasonic reaction for 2 h at room tempera ture, and 1 mL of water in which 20 μL of acetic acid was dissolved was added to quench the reaction.

After the reaction was complete, 5 μL of a sample was taken and identified by analytical HPLC. Parameters of the analytical HPLC on the Phenomenex Luna $C_{18}$ reversed-phase column (5 μm, 250×4.6 mm) were as follows: flow rate: 1 mL/min; phase A: a solution of 0.1% trifluoroacetic acid (TFA) in water; phase B: a solution of 0.1% TFA in acetonitrile; at 2 min to 25 min, decreasing from 95% to 20% in phase A and increasing from 5% to 80% in phase B; and at 25 min to 30 min, maintaining at 20% in phase A. The ultraviolet (UV) absorbance was measured at 214 nm and 254 nm to obtain a retention time of the product NOTA-FAPI-B. The product was then separated through preparative HPLC. The collected product was lyophilized to obtain a fluffy white powder.

A high-resolution mass spectrometer (HRMS) was used to determine the molecular ion peak of the synthesized product: HRMS: [M+H]+=937.384 (m/z), theoretical calc: 937.3842 ($C_{44}H_{54}F_2N_{10}O_9S$).

Nuclear magnetic resonance (NMR) data of the above compound were as follows:

$^1$H NMR (400 MHz, $D_2O$) δ:2.273 (S, 2H), 2.875-3.314 (m, 12H), 3.153-3.351 (m, 6H), 3.694-3.786 (m, 9H), 4.187-4.371 (m, 10H), 5.118-5.138 (s, 1H), 7.178-7.369 (m, 2H), 7.464-7.483 (m, 4H), 7.831-7.898 (t, 1H), 8.721-8.738 (m, 2H).

Each of NOTA-Bn-FAPI-4, (S)-NOTA-Bn-FAPI-2, and NOTA-Bn-FAPI-2 was prepared according to the above method.

Example 11

Preparation of an (S)—AlF-NOTA-Bn-FAPI-4 Control

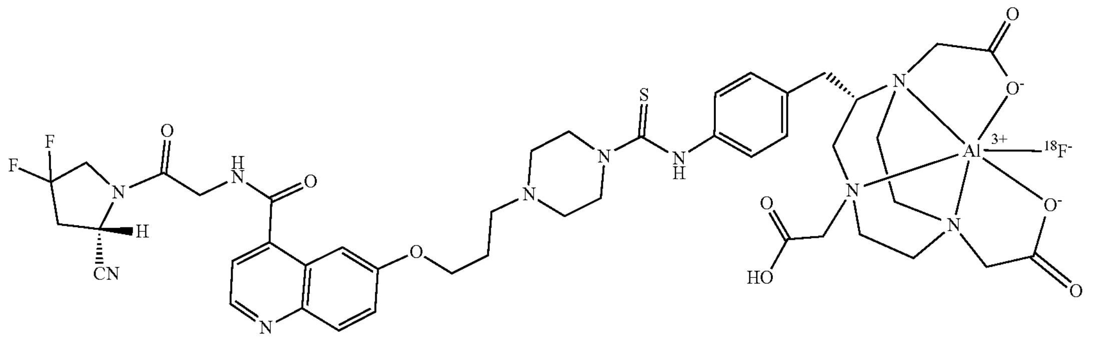

(S)-AlF-NOTA-Bn-FAPI-4

In a 1 mL V-reaction flask, a mixed solution of 7 μL of sodium fluoride (3.0 mM) and a sodium acetate buffer (0.1 M, pH 4.0) was added to a mixed solution of 0.2 mL of deionized water, 10 μL of aluminum trichloride (2 mM), and a sodium acetate buffer (0.1 M, pH 4.0). The resulting system was ultrasonically shaken for 1 min and heated to 100° C. to allow a reaction for 10 min. A mixed solution of 5 μL of acetonitrile, 5 μL of (S)-NOTA-Bn-FAPI-4 (2.5 mM), and a sodium acetate buffer (0.1 M, pH 4.0) was added, and the resulting system was further heated to 100° C. to allow a reaction for 10 min.

After the resulting reaction solution was cooled, 5 μL of a sample was taken and identified by analytical HPLC. Parameters of the analytical HPLC on the Phenomenex Luna $C_{18}$ reversed-phase column (5 μm, 250×4.6 mm) were as follows: flow rate: 1 mL/min; phase A: a solution of 0.1% TFA in water; phase B: a solution of 0.1% TFA in acetonitrile; at 2 min to 25 min, decreasing from 95% to 20% in phase A and increasing from 5% to 80% in phase B; and at 25 min to 30 min, maintaining at 20% in phase A. Single components were collected at 15.53 min and 15.72 min and analyzed by LC-MS: molecular ion peaks: $[M+H]^+$=964.371 (m/z), theoretical calc: 964.3717 ($C_{44}H_{54}AlF_2N_{10}O_9S$) corresponding to (S)—Al-NOTA-Bn-FAPI-4 (Rt=15.53 min) component; and $[M+H]^+$=983.371 (m/z) corresponding to (S)—AlF-NOTA-Bn-FAPI-4 (Rt=15.72 min), theoretical calc: 983.3701 ($C_{44}H_{54}AlF_3N_{10}O_9S$) component.

3 mL of the remaining reaction solution was taken and diluted with water, and the resulting diluted solution was allowed to pass through an $Al_2O_3$ column to obtain a filtrate. The filtrate was allowed to pass through a $C_{18}$-Plus column for enrichment. The column was washed with 3 mL of phosphate-buffered saline (PBS) and 2 mL of water and subjected to elution with 600 μL of a solution of 10 mM hydrochloric acid in ethanol. An eluate was allowed to pass through a sterile filtration membrane to obtain an injection for a tumor stroma diagnostic imaging experiment.

Each of AlF-NOTA-Bn-FAPI-4, (S)—AlF-NOTA-Bn-FAPI-2, and AlF-NOTA-Bn-FAPI-2 was prepared according to the above method.

Example 12

1. A Cell Binding Experiment of (S)—[$^{18}$F]—AlF-NOTA-Bn-FAPI-4

(S)—[$^{18}$F]—AlF-NOTA-Bn-FAPI-4 was adopted as an experimental group, AlF-FAPI-75+(S)—[$^{18}$F]—AlF-NOTA-Bn-FAPI-4 was adopted as a blockage group, and free $^{18}F^-$ was adopted as a control group.

A human fibrosarcoma cell HT-1080-FAP (HT-1080-FAP cell line) transfected by an FAP gene was activated to obtain an HT-1080-FAP cell suspension.

The experimental group: 2 mL of the HT-1080-FAP cell suspension was taken and washed three times with frozen PBS. A complete medium including the imaging agent (S)—[$^{18}$F]—AlF-NOTA-Bn-FAPI-4 (2.96 MBq, 80 μCi) was added, and the resulting mixture was incubated for 1 h. The cells were washed three times with frozen PBS, and 0.5 mL of NaOH-sodium dodecyl sulfate (SDS) (1M NaOH, 1% SDS) was added for lysis. The resulting cell lysate was finally collected, placed in a marked γ-counting tube, and subjected to γ-counting.

The blockage group: 2 mL of the HT-1080-FAP cell suspension was taken and washed three times with frozen PBS. A complete medium including the blocker AlF-FAPI-75 was added, and the resulting mixture was incubated for 0.5 h. A complete medium including the imaging agent (S)—[$^{18}$F]—AlF-NOTA-Bn-FAPI-4 (2.96 MBq, 80 μCi) was added, and the resulting mixture was incubated for 1 h. The cells were washed three times with frozen PBS, and 0.5 mL of NaOH-SDS (1 M NaOH, 1% SDS) was added for lysis. The resulting cell lysate was finally collected, placed in a marked γ-counting tube, and subjected to γ-counting.

The control group: 2 mL of the HT-1080-FAP cell suspension was taken and washed three times with frozen PBS. A complete medium including the free $^{18}F^{-}$ (2.96 MBq, 80 μCi) was added, and the resulting mixture was incubated for 1 h. The cells were washed three times with frozen PBS, and 0.5 mL of NaOH-SDS (1 M NaOH, 1% SDS) was added for lysis. The resulting cell lysate was finally collected, placed in a marked γ-counting tube, and subjected to γ-counting. The final volumes of the groups were the same. After 1 h of incubation, a radioactivity count value of cell uptake in each group was shown in Table 1.

TABLE 1

Radioactivity count values of the cell binding experiment of (S)—[$^{18}$F]—AlF-NOTA-Bn-FAPI-4

| Grouping for the cell binding experiment | Radioactivity count value (γ count value/min) |
|---|---|
| Experimental group | 5999.98 ± 864.12 |
| Blockage group | 2000.01 ± 113.34 |
| Control group | 180.13 ± 34.67 |

The above data shows that the absorption of tumor cells for a radiocontrast agent in the experimental group is 3 times that of the blockage group with a statistically significant difference (t=6.713, P<0.05) and the absorption of tumor cells for a radiocontrast agent in the experimental group is 33.31 times that of the control group with a statistically significant difference (t=8.934, P<0.01). It can be seen that the imaging agent (S)—[$^{18}$F]—AlF-NOTA-Bn-FAPI-4 shows prominent selective adsorption for tumor cells. Therefore, it can be determined that the contrast agent prepared in the present example exhibits prominent specificity in the diagnosis of FAP overexpression in tumor stroma.

2. Biodistribution of (S)—[$^{18}$F]—AlF-NOTA-Bn-FAPI-4 in Tumor-Bearing Mice

Six mice were divided into an experimental group and a blockage group with 3 mice in each group. Mice in the experimental group each were injected with (S)—[$^{18}$F]—AlF-NOTA-Bn-FAPI-4 (3.7 MBq, 100 μCi) through a tail vein within 1 min, and 60 min later, the mice each were sacrificed by cutting a carotid artery for bloodletting. Mice in the blockage group each were injected with 100 μg of the blocker AlF-FAPI-75 (1,000 μg/mL) through a tail vein and injected with (S)—[$^{18}$F]—AlF-NOTA-Bn-FAPI-4 (3.7 MBq, 100 μCi) through a tail vein 30 min later, and 60 min later, the mice each were sacrificed by cutting a carotid artery for bloodletting. The heart, liver, lung, kidney, spleen, brain, and the like were collected, weighed, and tested for radioactivity. Finally, an (S)—[$^{18}$F]—AlF-NOTA-Bn-FAPI-4 radioactivity uptake rate (a percentage of uptake radioactivity per gram of tissue in the injected radioactivity, ID/g) in each of blood and various organs and a radioactivity ratio of a target organ to a non-target organ (T/NT) were calculated at different time points. The final results are shown in Table 2.

TABLE 2

Distribution of (S)—[$^{18}$F]—AlF-NOTA-Bn-FAPI-4 in tumor-bearing mice 1 h after injection, % ID/g

| Tissue or organ | Grouping | |
|---|---|---|
| | Experimental group | Blockage group |
| Blood | 0.10 + 0.04 | 0.13 ± 0.10 |
| Heart | 0.09 + 0.09 | 0.08 ± 0.05 |
| Liver | 0.07 + 0.05 | 0.08 ± 0.04 |
| Spleen | 0.10 + 0.01 | 0.16 ± 0.14 |
| Kidney | 0.94 + 0.20 | 0.84 ± 0.21 |
| Muscle | 0.16 + 0.05 | 0.09 ± 0.03 |
| Bone | 0.15 + 0.03 | 0.06 ± 0.01 |
| Intestine | 0.19 + 0.06 | 0.16 ± 0.02 |
| Brain | 0.02 + 0.01 | 0.03 ± 0.01 |
| Lung | 0.16 + 0.08 | 0.28 ± 0.19 |
| Tumor | 1.12 + 0.06 | 0.22 ± 0.05 |

It can be seen from Table 2 that, according to the biological distribution of (S)—[$^{18}$F]—AlF-NOTA-Bn-FAPI-4 in the experimental group and the blockage group 1 h after injection, blood uptake values of the experimental group and the blockage group are (0.10±0.04)% ID/g and (0.13±0.10)% ID/g, respectively, indicating that (S)—[$^{18}$F]—AlF-NOTA-Bn-FAPI-4 is quickly cleared in the blood; kidney uptake values of the experimental group and the blockage group are (0.94±0.20)% ID/g and (0.84±0.21)% ID/g, respectively, indicating that the marker is mainly excreted by the kidney; radioactivity uptake values of graft tumors in the experimental group and the blockade group are (1.12±0.06)% ID/g and (0.22±0.05)% ID/g, respectively, with a statistically significant difference (t=2.921, P<0.05); and the distribution of (S)—[$^{18}$F]—AlF-NOTA-Bn-FAPI-4 in other organs is significantly lower than that in tumors, indicating that the (S)—[$^{18}$F]—AlF-NOTA-Bn-FAPI-4 prepared in the present example exhibits prominent specificity and sensitivity for FAP overexpression in a tumor stroma.

The examples are described above to facilitate the comprehension and use of the present disclosure by those of ordinary skill in the art. Obviously, those skilled in the art can easily make various modifications to these examples and apply a general principle described herein to other examples without creative efforts. Therefore, the present disclosure is not limited to the above examples. All improvements and modifications made by a person skilled in the art according to the disclosure of the present disclosure should fall within the protection scope of the present disclosure.

What is claimed is:

1. A tumor stroma imaging agent with a chemical structural formula as follows:

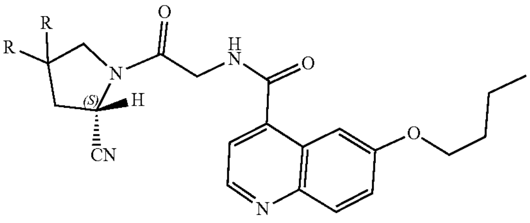

-continued

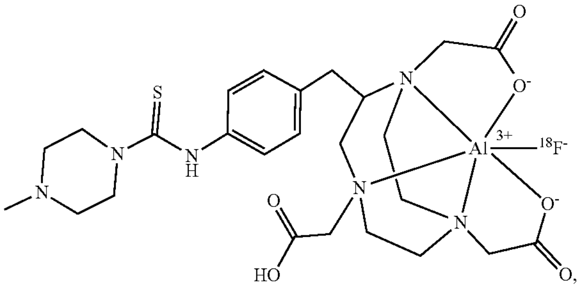

wherein R is hydrogen or fluorine.

2. The tumor stroma imaging agent according to claim 1, wherein the tumor stroma imaging agent has a chemical structural formula as follows:

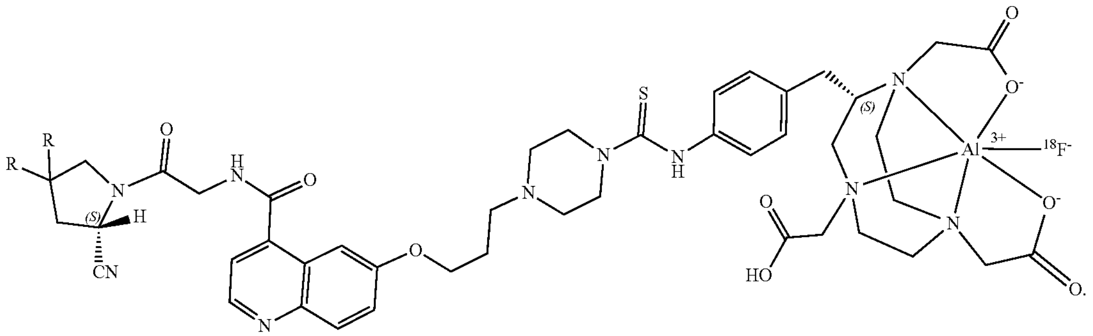

3. The tumor stroma imaging agent according to claim 1, wherein the tumor stroma imaging agent has a chemical structural formula selected from the group consisting of formula I

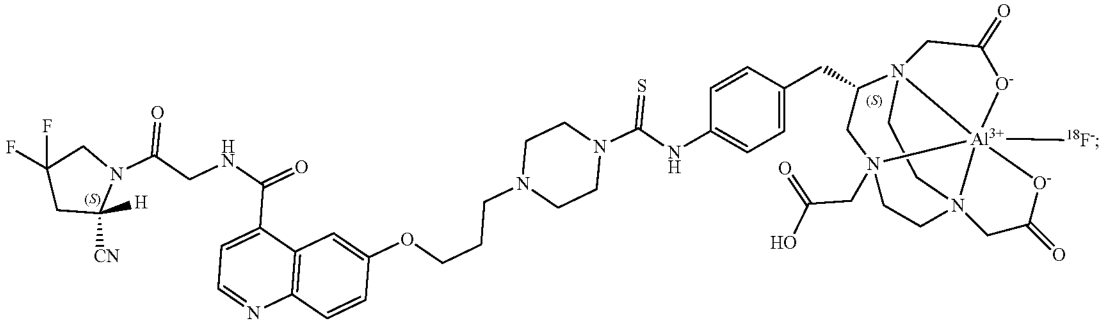

formula II

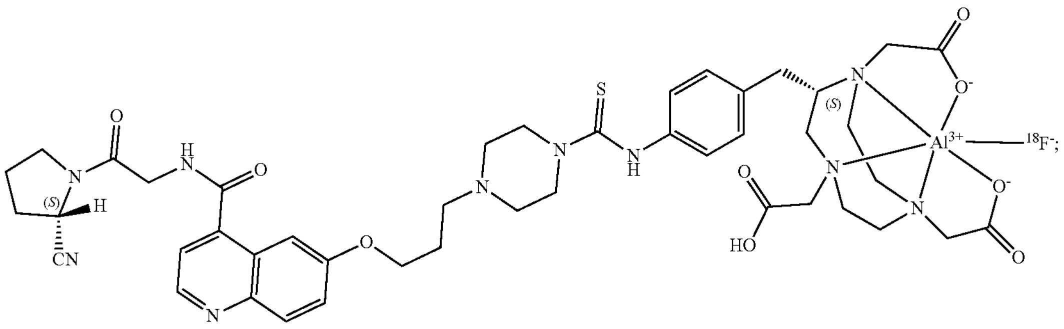

-continued formula III

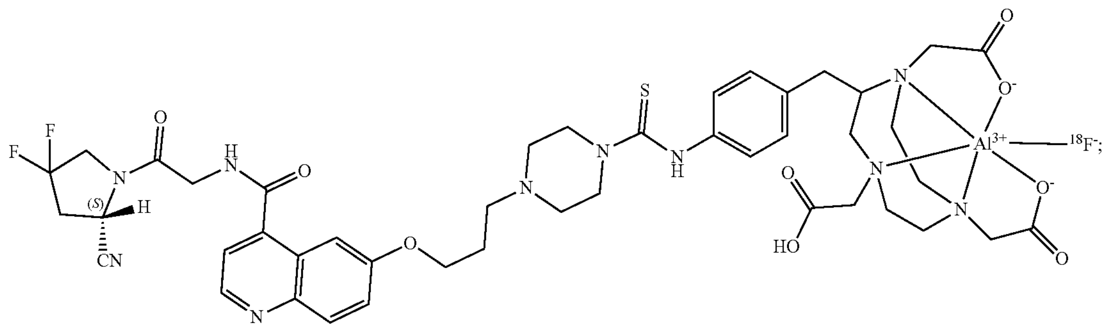

and formula IV

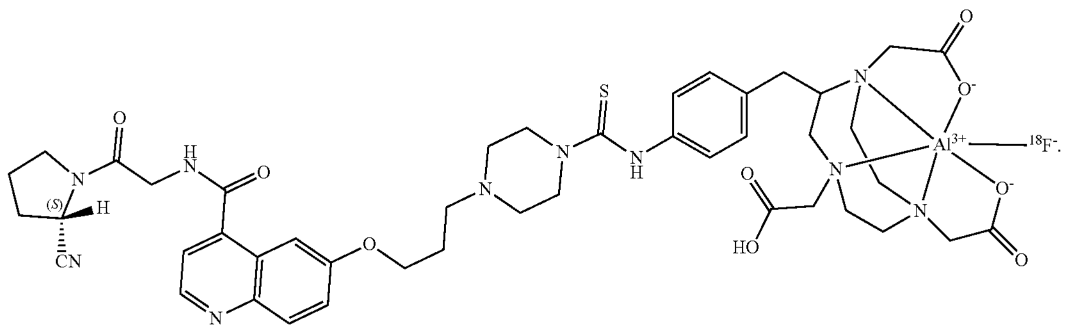

.

4. A preparation method of the tumor stroma imaging agent according to claim 1, comprising:

mixing an $^{18}F^-$-containing acetic acid-sodium acetate buffer with a labeling precursor, a solvent, and an $AlCl_3$ aqueous solution to allow a labeling reaction; and subjecting a product of the labeling reaction to a post-treatment, wherein the labeling precursor has a chemical structural formula as follows:

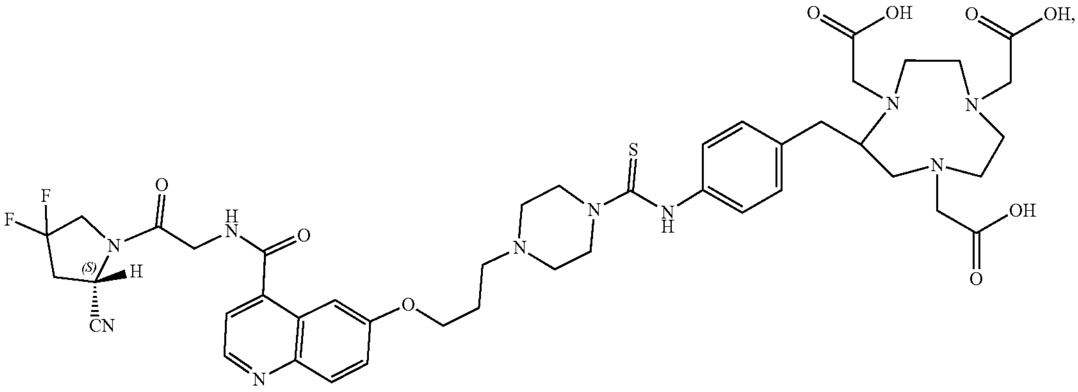

, or the labeling precursor is a salt

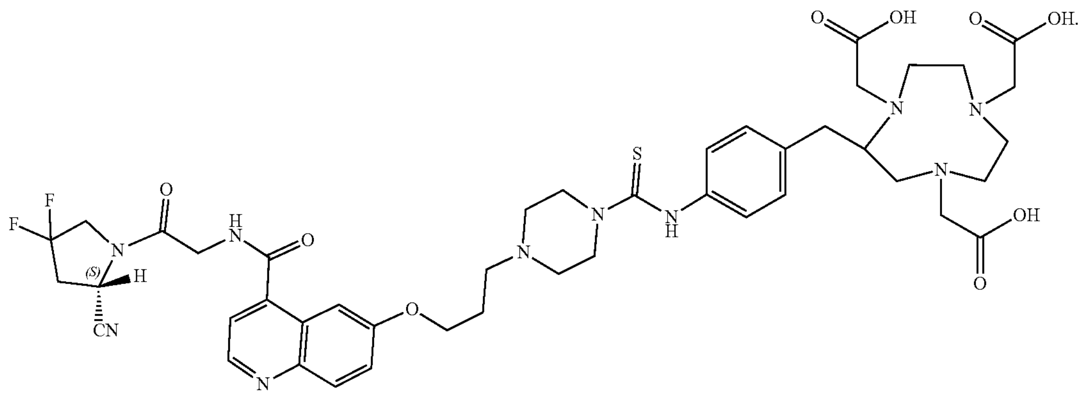

5. The preparation method according to claim 4, wherein the $^{18}F^{-}$-containing acetic acid-sodium acetate buffer has an activity of 110 mCi to 135 mCi.

6. The preparation method according to claim 4, wherein the $^{18}F^{-}$-containing acetic acid-sodium acetate buffer has a pH of 4.2.

7. The preparation method according to claim 4, wherein the labeling reaction is conducted at 80° C. to 120° C. for 5 min to 10 min.

8. The preparation method according to claim 5, wherein a volume-mass ratio of the $^{18}F^{-}$-containing acetic acid-sodium acetate buffer to the labeling precursor is 1:(0.9-1.6) mL/mg; the $^{18}F^{-}$-containing acetic acid-sodium acetate buffer, the solvent, and the $AlCl_3$ aqueous solution are in a volume ratio of (45-30):75:5; the $AlCl_3$ aqueous solution has a concentration of 0.4 M; and the solvent is selected from the group consisting of acetonitrile, N,N-dimethylformamide (DMF), dimethylsulfoxide (DMSO), and polyethylene glycol (PEG).

9. The preparation method according to claim 4, wherein the post-treatment comprises:

adding water to quench the labeling reaction and allowing a resulting reaction solution to pass through an $Al_2O_3$ column to obtain a filtrate; and allowing the filtrate to pass through a $C_{18}$-Plus column, rinsing the $C_{18}$-Plus column with ethanol and normal saline (NS) successively, and allowing an eluate to pass through a sterile filtration membrane to obtain an injection of the tumor stroma imaging agent.

10. The preparation method according to claim 9, wherein the injection has an activity of 50.3 mCi to 72.3 mCi.

11. The preparation method according to claim 4, wherein the labeling precursor has a chemical structural formula as follows:

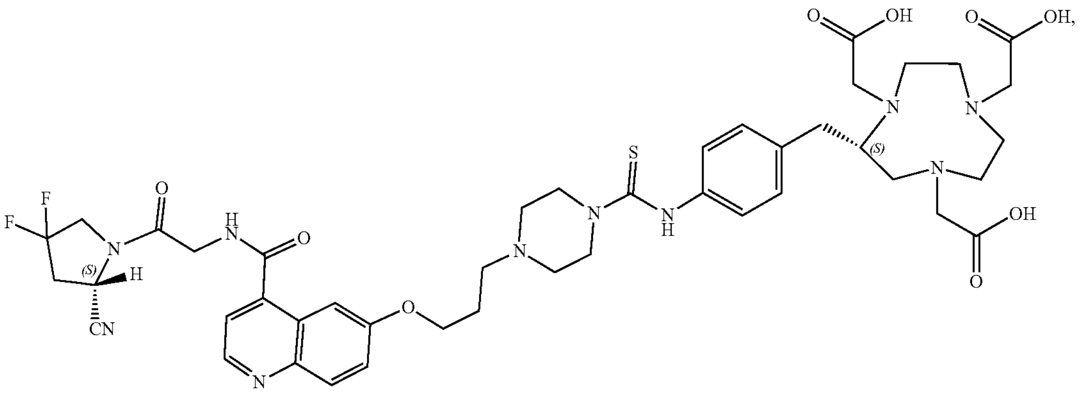

or the labeling precursor is a salt of
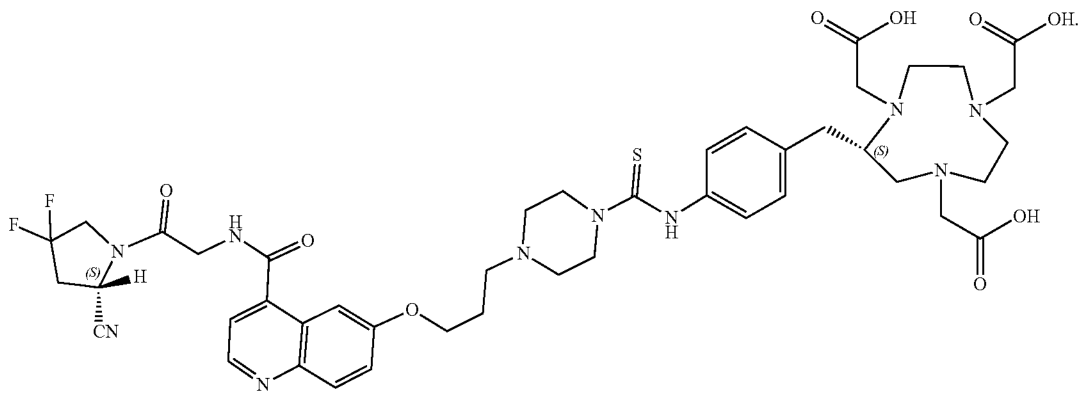
12. The preparation method according to claim 4, wherein the tumor stroma imaging agent has a chemical structural formula as follows:
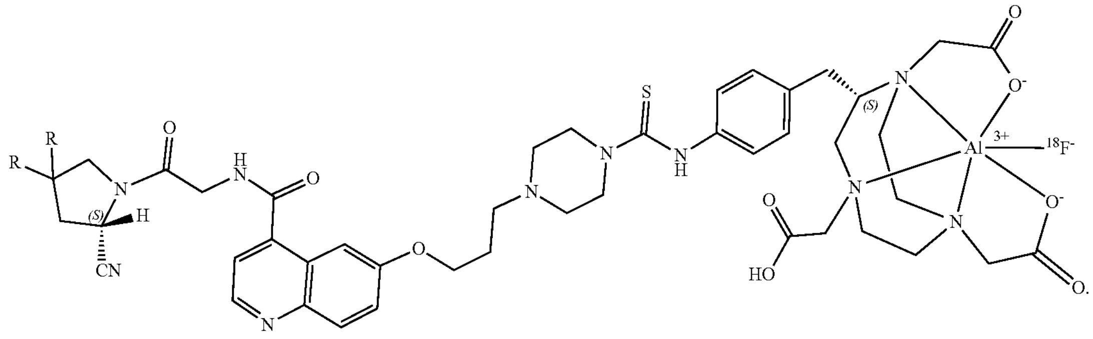
13. The preparation method according to claim 4, wherein the tumor stroma imaging agent has a chemical structural formula selected from the group consisting of
formula I
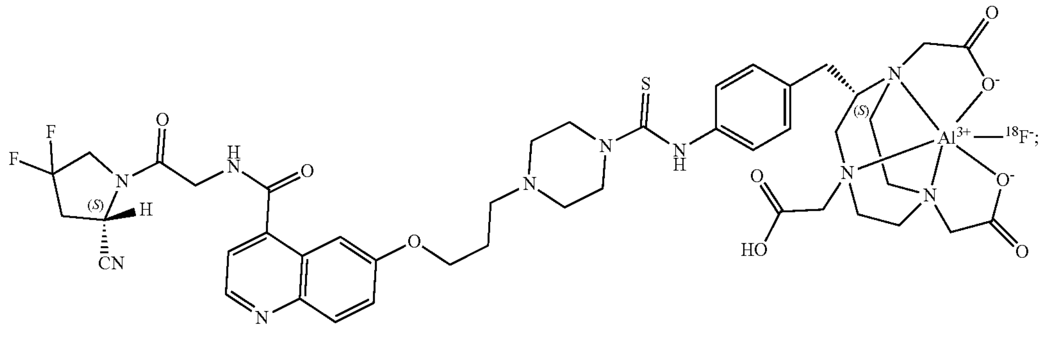

-continued
formula II
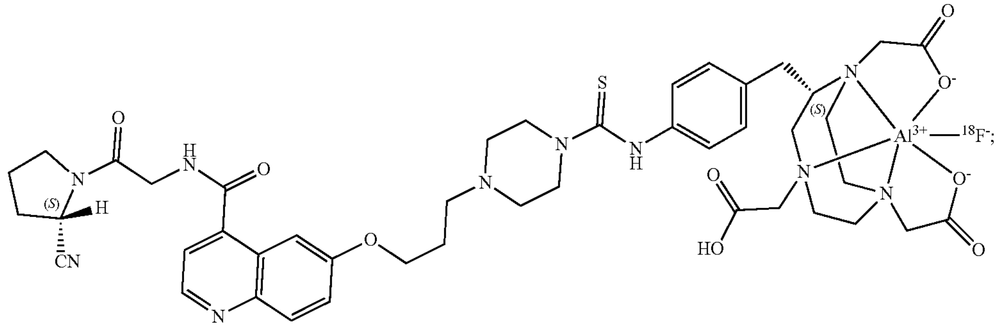
formula III
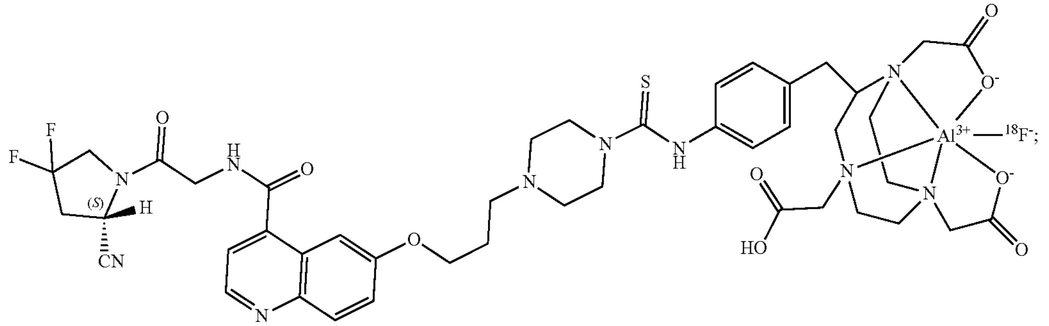
and
formula IV
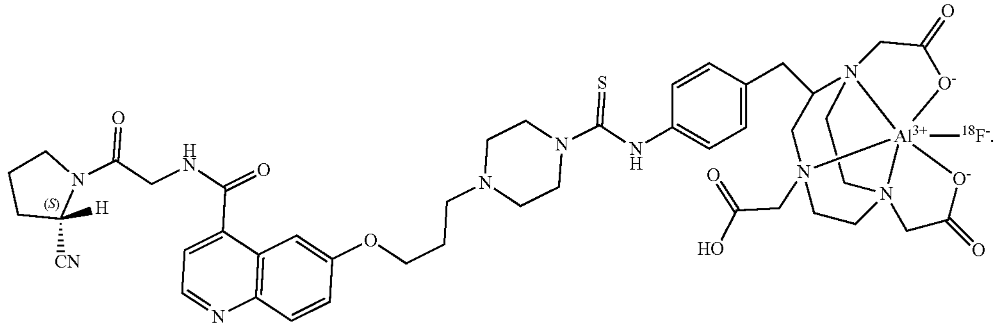
14. The preparation method according to claim 5, wherein the $^{18}F^-$-containing acetic acid-sodium acetate buffer has a pH of 4.2.
15. The preparation method according to claim 5, wherein the labeling reaction is conducted at 80° C. to 120° C. for 5 min to 10 min.
* * * * *